(12) United States Patent
Strickland et al.

(10) Patent No.: US 6,465,690 B1
(45) Date of Patent: Oct. 15, 2002

(54) PROCESS FOR THE PREPARATION OF POLYAMINO SUCCINIC ACIDS AND DERIVATIVES THEREOF

(75) Inventors: Alan D. Strickland; David A. Wilson; Brian D. Burkholder; Druce K. Crump, all of Lake Jackson, TX (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/511,404

(22) Filed: Feb. 23, 2000

Related U.S. Application Data

(60) Provisional application No. 60/126,402, filed on Mar. 26, 1999.

(51) Int. Cl.$^7$ .............................................. C07C 51/00
(52) U.S. Cl. ..................................................... 562/515
(58) Field of Search ......................................... 562/565

(56) References Cited

U.S. PATENT DOCUMENTS 2,761,874 A    9/1956  Bersworth et al. .......... 260/534

FOREIGN PATENT DOCUMENTS

| GB | 757705 | 9/1956 | |
|---|---|---|---|
| JP | 57-116031 | 7/1982 | ......... C07C/101/20 |
| WO | 97/08287 | 3/1997 | ............ C11D/3/33 |

OTHER PUBLICATIONS

*Chemical Abstract 98:54482 (JP 57–116031).
Tiedje, "Microbial Degradation of Ethylenediaminetetraacetate in Soils and Sediments," *Applied Microbiology*, Aug. 1975, pp. 327–329.
International Search Report dated May 30, 2000 issued by the EPO acting as the International Searching Authority in PCT/US00/04031.

*Primary Examiner*—Gary Geist
*Assistant Examiner*—Zachary C. Tucker

(57) ABSTRACT

A process for preparing polyamino monosuccinic acids, salts or chelates thereof by (a) reacting a maleic or fumaric acid ester or mixtures thereof with a polyamino compound in a primary alcohol as a solvent, (b) hydrolyzing the product obtained in step (a), and (c) separating the primary alcohol. The use of a primary alcohol as the solvent results in a markedly purer polyamino monosuccinic acid product and simpler reaction conditions than when the solvent is a secondary or tertiary alcohol.

21 Claims, No Drawings

PROCESS FOR THE PREPARATION OF POLYAMINO SUCCINIC ACIDS AND DERIVATIVES THEREOF

This application claims the benefit of U.S. Provisional Application No. 60/126,402, filed Mar. 26, 1999.

This invention relates to a process for the preparation of polyamino succinic acids and derivatives thereof in which process a primary alcohol is used as a solvent. In particular, this invention relates to a process for the preparation of ethylenediamine monosuccinic acid, its salts or chelates, its esters, and its lactams.

BACKGROUND OF THE INVENTION

Chelants or chelating agents are compounds which form coordinate covalent bonds with a metal ion to form chelates. Chelates are coordination compounds in which a central metal atom is bonded to two or more other atoms in at least one other molecule (called ligand) such that at least one heterocyclic ring is formed with the metal atom as part of each ring.

Chelants are used in a variety of applications including food processing, soaps, detergents, cleaning products, personal care products, pharmaceuticals, pulp and paper processing, gas conditioning, water treatment, metalworking and metal plating solutions, textile processing solutions, fertilizers, animal feeds, herbicides, rubber and polymer chemistry, photofinishing, and oil field chemistry. Some of these activities result in chelants entering the environment. For instance, agricultural uses or detergent uses may result in measurable quantities of the chelants being present in water. It is, therefore, desirable that chelants degrade after use.

Biodegradability, that is susceptibility to degradation by microbes, is particularly useful because the microbes are generally naturally present in environments into which the chelants may be introduced. Commonly used chelants like ethylenediamine tetraacetic acid (EDTA) are biodegradable, but at rates somewhat slower and under conditions considered by some to be less than optimum. (See, for example, Tiedje, "Microbial Degradation of Ethylenediaminetetraacetate in Soils and Sediments," Applied Microbiology, August 1975, pp. 327–329.)

It would be desirable to have a chelant useful in areas such as those mentioned above wherein such chelant is greater than about 60 percent biodegradable within less than 28 days according to the OECD 301B Modified Sturm Test or greater than about 80 percent biodegradable within less than 28 days according to the Semicontinuous Activated Sludge Test (ASTM D 2667 89).

It has been found that racemic ethylenediamine monosuccinic acid (EDMS); also named N-(2-aminoethyl) aspartic acid (AEA), and its salts are excellent chelants and are readily biodegradable. Several chelates of EDMS are also readily biodegradable and in some cases may readily exchange their metals for other metals. These chelates have the advantage of forming non-hygroscopic solids. Since EDMS and its salts and chelates are quite useful in the applications mentioned above, it would be advantageous to have a simple and economical process for producing these compounds.

British Patent No. 757,704 and U.S. Pat. No. 2,761,874, both by Bersworth, teach the preparation of EDMS by dissolving ethylenediamine in tetiary butanol and slowly adding diethyl maleate while keeping the temperature below 50° C., preferably below 35° C. The lower temperature was necessary to reduce the production of undesired byproducts. The resulting diethyl ester of EDMS is then hydrolyzed with sodium hydroxide to give disodium EDMS. This method of production is cumbersome and expensive.

Japanese Patent Application Kokai No. 57116031 A2 (Tokyo Organic Chemical Industries, Ltd.), Chemical Abstracts Number 98:54482, teaches that disodium EDMS can be prepared by refluxing sodium maleate hydrate (89 g, 0.50 mole if monohydrate, 0.45 mole if dihydrate) in water with 250 ml (224.9 g, 3.74 mole) ethylenediamine for 8.5 hours to produce 125 g (0.57 mole) disodium EDMS. Attempts to reproduce this preparation have failed to produce pure EDMS. Significant contamination with tetrasodium ethylenediamine disuccinate (EDDS) is present.

J. Am. Chem. Soc. 1984, 106, 2819–2837 reports the preparation of (R)-N-(2-aminoethyl) aspartic acid and (S)-N-(2-aminoethyl) aspartic acid in small quantities. These compounds are prepared by reacting maleic acid (18 g) with [Co(en)$_2$CO$_3$]Br (50 g) in one liter of boiling water, concentrating this to 100 ml, crystallizing overnight, washing the resulting crystals first with methanol/water and then with methanol. The crystals (9.9 g) are then dissolved in 50 ml boiling water and reacted with 17 g NaClO$_4$H$_2$O, and the product crystallized by cooling to 0° C. The crystallization procedure was repeated, and the crystals (7.7 g) washed with methanol. The washed crystals (3.9 g) were placed in 100 ml liquid ammonia and swirled with 0.2 g NaNH$_2$ for two minutes followed by quenching with 2 g ammonium bromide and suspension in 15 ml of 1 M perchloric acid, filtration, recrystallization from 25 ml boiling water with addition of 1 g sodium perchlorate and 5 ml ethanol to produce 1.9 g solid. This solid is then dissolved in 41 ml of water and treated with H$_2$S, sorbed onto an acid loaded AG 50W-X2 resin column (4.5×10 cm), rinsed with 14 ml water, and eluted with aqueous ammonium hydroxide, concentrated, and crystallized with addition of methanol. After redissolution in water, recrystallization with ethanol, and drying over P$_4$O$_{10}$ in vacuo, 0.62 g of N-(2-aminoethyl) aspartic acid was isolated for an overall yield of 4.4 percent. This poor yield would make the preparation too expensive as an industrial process.

Since polyamino monosuccinic acids such as EDMS and derivatives thereof are desirable products, there is a great need and interest in the industry for a simple process for the manufacture thereof which process is more economical than known processes.

It has been surprisingly discovered that reacting a maleate or fumarate dialkyl ester, such as, for example, dimethyl maleate, with a polyamino compound, such as ethylenediamine, results in markedly purer polyamino monosuccinic acid product and simpler reaction conditions when the solvent for the reaction is a primary alcohol rather than the solvents currently used or described in the literature.

SUMMARY OF THE INVENTION

The present invention concerns a process for preparing a polyamino monosuccinic acid, a salt or chelate thereof comprising (a) reacting a diester of maleic or fumaric acid or a mixture thereof with a polyamino compound in a primary alcohol as a solvent;

(b) hydrolyzing the product obtained in step (a); and (c) separating the primary alcohol.

DETAILED DESCRIPTION OF THE INVENTION

The present invention provides a simple, convenient and more economical way to prepare a polyamino monosuccinic acid, a salt or chelate thereof. It has been surprisingly discovered that reacting an ester of maleic or fumaric acid with a polyamino compound in a primary alcohol solvent to produce the monoalkyl ester of polyamino monosuccinic lactam followed by hydrolysis with a hydroxide or oxide of an alkali metal or an alkaline earth metal results in a product with fewer side products than when secondary or tertiary alcohols are used as the solvent and does not require cooling of the reaction vessel.

The use of the primary alcohols, rather than the tertiary butanol described in the literature, allows the reaction of alkylenediamine and dialkyl maleate or dialkyl fumarate to be run at ambient temperature and produces purer product (less EDDS, maleate, and fumarate contamination).

The hydrolysis in step (b) of the present process is a well known process and it can be performed under either alkaline or acidic conditions. when the hydrolysis is performed under alkaline conditions, it is usually performed under aqueous conditions with a metal oxide or metal hydroxide. The preferred metal oxides and metal hydroxides are oxides and hydroxides of alkali metals and alkaline earth metals. Sodium hydroxide and potassium hydroxide are particularly preferred metal hydroxides.

When the hydrolysis is performed under acidic conditions, it is usually performed under aqueous conditions. Sulfuric and hydrochloric acids are particularly preferred acids.

The separation of the primary alcohol solvent from the polyamino monosuccinic acid product in step (c) of the present process can be performed using any conventional separation method such as, for example, extraction, distillation, evaporation under vacuum and the like methods. If desired, the primary alcohol separated in step (c) can be recycled to step (a) of the present process. The separation of the primary alcohol solvent can also be performed during the hydrolysis in step (b) of the present process.

Any lower alkyl ester of maleic or fumaric acid or a mixture thereof is suitable for use in the present invention. As used herein, "lower alkyl" means an alkyl group having from 1 to 6, preferably, from 1 to 4, most preferably from 1–2, carbon atoms.

Non-limiting examples of suitable lower alkyl esters of maleic acid include, for example, dimethyl maleate, diethyl maleate, dipropyl maleate, dibutyl maleate, methyl ethyl maleate, methyl propyl maleate, methyl butyl maleate, ethyl propyl maleate, ethyl butyl maleate, propyl butyl maleate, mixtures thereof and the like.

Non-limiting examples of suitable lower alkyl esters of fumaric acid include, for example, dimethyl fumarate, diethyl fumarate, dipropyl fumarate, dibutyl fumarate, methyl ethyl fumarate, methyl propyl fumarate, methyl butyl fumarate, ethyl propyl fumarate, ethyl butyl fumarate, propyl butyl fumarate, mixtures thereof and the like.

Any polyamino compound such as, for example, diamino and triamino compounds, can be used in the present invention provided that they contain at least one reactive amino hydrogen. Alkylenediamines are preferred polyamino compounds. Non-limiting examples of suitable alkylenediamines include ethylenediamine, 1,6-hexamethylenediamine, 1,2-propylenediamine, 1,3-propylenediamine, cis-cyclohexanediamine, and trans-cyclohexanediamine.

Any primary alcohol having from 1 to 6, preferably from 1 to 4, most preferably from 1 to 2, carbon atoms or a mixture of two or more such primary alcohols is suitable for use as a solvent in the present invention. Non-limiting examples of suitable primary alcohols include, for example, methanol, ethanol, 1-propanol, 1-butanol, 1-pentanol, 1-hexanol, any mixture thereof and the like. Methanol, ethanol, 1-propanol, 1-butanol and a mixture thereof are preferred. The economical availability of methanol and ethanol make them particularly desirable for use as solvents in this reaction. Methanol is particularly useful since it does not form an azeotropic mixture with water and can be easily distilled from the final reaction mixture after the addition of aqueous alkali solutions used for hydrolysis of the addition product.

It has been surprisingly discovered that the reaction of an ester of maleic or fumaric acid in primary alcohol as a solvent requires much less stringent reaction conditions than the same reaction using a tertiary alcohol as a solvent as is described in the literature. For example, the reaction of dimethyl maleate with ethylenediamine in tertiary butanol requires careful control of the reaction conditions. The reaction must proceed with addition of dimethyl maleate to a solution of ethylenediamine in tertiary butanol over a prolonged time to permit removal of the heat produced by the exothermic reaction. If the temperature during the addition of the dimethyl maleate is ever allowed to rise above 35° C., the EDMS produced will be contaminated with more than 5% ethylenediamine disuccinic acid (EDDS). Controlling the temperature to prevent the reaction from ever exceeding 20° C. is necessary to approach a 1% EDDS contamination. Keeping the temperature below 15° C. is required to routinely prepare EDMS with less than 1% EDDS contaminant. However, the freezing point of tertiary butanol is 26° C., so the reaction mixture is quite viscous at temperatures required to produce pure EDMS. The order of addition of materials when tertiary butanol is used as solvent is important because it significantly affects the purity of the product.

By contrast, in the process of the present invention, the rate of addition of the materials is not important and the order of addition of the materials can be altered. Thus, the reaction in a primary alcohol can be performed with addition of dimethyl maleate to a solution of ethylenediamine or, alternatively, the addition of ethylenediamine to a solution of dimethyl maleate without significant change in the purity of the EDMS isolated. The addition rate can be determined by the speed at which the liquids can be mixed and the boiling point of the solvent rather than by trying to minimize the temperature increase caused by the heat being produced. Since methanol is much less viscous than tertiary butanol, the liquids can be mixed more efficiently and with less energy expenditure.

In the process of the present invention, the primary alcohol to be used as the solvent can also be used to react with maleic anhydride, maleic acid, or fumaric acid to produce the diester. This diester can then be used to react with the polyaminoalkyl compound using the same primary alcohol as the solvent. After the addition reaction has produced the ester form of the polyamino monosuccinate, hydrolysis by either acidic or basic means can be performed easily with recovery of the primary alcohol both from the solvent and from the alcohol produced during hydrolysis. This primary alcohol may then be recycled into subsequent runs of the process without the need to fractionally distill two different alcohols. This is an improvement over using tertiary or secondary alcohols as the solvent since these do not readily form diesters with maleate or fumarate. Use of these alcohols as solvent would require separation of the alcohol used as solvent from the alcohol used to form the diester.

The process can be run as a batch reaction or as a continuous reaction.

If desired, the preparation of dialkyl maleate or dialkyl fumarate can be made an integral part of the present process. Dialkyl maleate and dialkyl fumarate can be prepared by any of various known methods. Acid catalysis of the reaction of alkyl alcohols with carboxylic acids, anhydrides, or salts of carboxylic acids with concomitant removal of the water produced during esterification is often used for the preparation of dialkyl esters. The acid catalyst is preferably a cationic exchange resin such as Dowex® MSC-1 resin or Nafion® resin in the acid form. The choice of the acid catalyst for the esterification of maleic anhydride, maleic acid, or salts of maleic acid is critical to the process. Use of a liquid acid requires removal of the acid from the final product, for example, by distillation of the dialkyl ester which typically requires temperatures around 200° C. Use of a solid acid or Lewis acid can permit separation of the catalyst from the dialkyl ester by filtration. The choice of acid also affects the ratio between dialkyl maleate esters and dialkyl fumarate esters. Sulfuric acid favors maleate esters while hydrochloric acid favors fumarate esters.

Similarly, maleic anhydride, maleic acid, or maleate salts can be reacted with alkyl alcohols. Separation of water can be accomplished by fractional distillation of the reaction mixture, passing the vapor from the reaction through a dehydrating agent, or otherwise heating the reaction mixture above 100° C. to remove water and varying amounts of the alcohol and the esters.

Reactive distillation is another known method for forming the dialkyl ester from maleic anhydride. In this technique, the alcohol is placed in a vessel and heated to boiling with vapors being directed into a distillation tower charged with the acid catalyst and maintained above 100° C. Maleic anhydride is melted and directed into the top of the distillation tower. The resulting dialkyl ester is collected in the bottom vessel while water is recovered at the top of the distillation tower. Modifications are possible, including fractional distillation of water and excess alcohol from the top of the distillation tower, reacting maleic anhydride with an equimolar quantity of the alkyl alcohol before directing it into the tower, using maleic acid in place of maleic anhydride, and other such variations as will be obvious to those skilled in the art.

The following examples are provided to more fully illustrate the present invention but are not intended to be, nor should they be construed as being, limiting in any way of the scope of the invention.

COMPARATIVE EXAMPLE A

Ethylenediamine (1 mole, 60.1 g) is dissolved in tertiary butanol (500 ml) with vigorous stirring using a magnetic stir bar in a 1 liter round bottomed flask. Dimethyl maleate (1 mole, 144.1 g) is added over approximately 2 minutes. The reaction in allowed to continue overnight. Sodium hydroxide solution (160.0 g of 50% solution) is added to the flask. The reaction mixture is heated and then the alcohols are removed by evaporation under vacuum. The resulting product was analyzed by liquid chromatography and was found to have 85.8 percent disodium EDMS and 14.2 percent tetrasodium EDDS.

COMPARATIVE EXAMPLE B

Ethylenediamine (1 mole, 60.1 g) is dissolved in 2-butanol (500 ml) with vigorous stirring using a magnetic stir bar in a 1 liter round bottomed flask. Dimethyl maleate (1 mole, 144.1 g) is added over approximately 2 minutes. The reaction is allowed to continue overnight. Sodium hydroxide solution (160.0 g of 50% solution) is added to the flask. The reaction mixture is heated and then the alcohols are removed by evaporation under vacuum. The resulting product was analyzed by liquid chromatography and was found to have 84 percent disodium EDMS and 16 percent tetrasodium EDDS.

COMPARATIVE EXAMPLE C

Ethylenediamine (1 mole, 60.1 g) is dissolved in 2-propanol (500 ml) with vigorous stirring using a magnetic stir bar in a 1 liter round bottomed flask Dimethyl maleate (1 mole, 144.1 g) is added over approximately 2 minutes. The reaction is allowed to continue overnight. Sodium hydroxide solution (160.0 g of 50% solution) is added to the flask. The reaction mixture is heated and then the alcohols are removed by evaporation under vacuum. The resulting product was analyzed by liquid chromatography and was found to have 87.1 percent disodium EDMS and 12.9 percent tetrasodium EDDS.

Example 1

Ethylenediamine (1 mole, 60.1 g) is dissolved in methanol (500 ml) with vigorous stirring using a magnetic stir bar in a 1 liter round bottomed flask. Dimethyl maleate (1 mole, 144.1 g) is added over approximately 2 minutes. The reaction is allowed to continue overnight. Analysis by nuclear magnetic resonance at this time indicates the formation of the monomethyl ester of EDMS lactam (CAS 89852-17-5) Sodium hydroxide solution (160.0 g of 50% solution) is added to the flask. The reaction mixture is heated and then the alcohol is removed by evaporation under vacuum. The resulting product was analyzed by liquid chromatography and was found to have 98.8 percent disodium EDMS and 1.2 percent tetrasodium EDDS.

Example 2

Ethylenediamine (1 mole, 60.1 g) is dissolved in ethanol (500 ml) with vigorous stirring using a magnetic stir bar in a 1 liter round bottomed flask. Dimethyl maleate (1 mole, 144.1 g) is added over approximately 2 minutes. The reaction is allowed to continue overnight. Sodium hydroxide solution (160.0 g of 50% solution) is added to the flask. The reaction mixture is heated and then the alcohols are removed by evaporation under vacuum. The resulting product was analyzed by liquid chromatography and was found to have 95.7 percent disodium EDMS and 4.3 percent tetrasodium EDDS.

Example 3

Ethylenediamine (1 mole, 60.1 g) is dissolved in 1-butanol (500 ml) with vigorous stirring using a magnetic stir bar in a 1 liter round bottomed flask. Dimethyl maleate (1 mole, 144.1 g) is added over approximately 2 minutes. The reaction is allowed to continue overnight. sodium hydroxide solution (160.0 g of 50% solution) is added to the flask. The reaction mixture is heated and then the alcohols are removed by evaporation under vacuum. The resulting product was analyzed by liquid chromatography and was found to have 93.2 percent disodium EDMS and 6.8 percent tetrasodium EDDS.

Example 4

Methanol (500 ml, 390 g) and ethylenediamine (1 mole, 60.1 g) are mixed and allowed to cool to room temperature.

Dimethyl maleate (1 mole, 144.1 g) is added slowly with stirring using a magnetic stir bar. The reaction mixture is stirred and kept at room temperature. The reaction mixture is diluted with methanol to a weight of 600 g. An aliquot of 200 g of the reaction mixture is placed in a flask and mixed with calcium oxide (0.33 mole, 18.7 g) and water (3 mole, 53.4 g). The solution is then evaporated to dryness on a rotary evaporator at 100° C. The resulting solid is easily stored as a dry powder.

Example 5

Methanol (500 ml, 393 g) and ethylenediamine (1 mole, 60.1 g) are mixed. Dimethyl maleate (1 mole, 144.1 g) is added slowly with vigorous stirring. An aliquot of 295 g of the reaction mixture is placed in a flask and evaporated under vacuum to remove all methanol. The resultant 85.1 g of liquid is cooled from 80° C. to room temperature where it solidifies. It is mixed with potassium hydroxide (0.99 mole, 121.6 g of 45.7% solution) and water. The solution is then evaporated on a rotary evaporator at 100° C. No solid formed, even when no further water or methanol could be removed. The resulting dipotassium EDMS is stored at room temperature.

Example 6

Methanol (500 ml, 390 g) is placed into a reaction vessel. Ethylenediamine (1 mole, 60.1 g) is mixed into the methanol and the solution cooled to −4° C. Dimethyl maleate (1 mole, 144.1 g) is slowly dripped into the ethylenediamine solution while keeping the temperature below 10° C. The reaction is continued overnight. The reaction mixture formed fine crystals of the product, but remained quite fluid with no difficulty in stirring. The resultant mixture is hydrolyzed with sodium hydroxide solution (2 mole, 160.0 g, 50%) and then methanol is removed by evaporation. Analysis by liquid chromatography revealed that the product is 99.5 percent disodium EDMS and 0.5 percent tetrasodium EDDS with no maleate present.

Example 7

Methanol (32 ml, 25.0 g) is placed into a 100 ml reaction vessel and mixed with ethylenediamine (0.019 mole, 1.16 g) and dimethyl fumarate (0.019 mole, 2.78 g). The reaction mixture is stirred for 16 hours. The resultant reaction mixture is then hydrolyzed with a solution of sodium hydroxide (0.038 mole, 3.09 g, 50%) followed by removal of methanol by evaporation. Analysis by liquid chromatography revealed that the product is 99.6 percent disodium EDMS and 0.4 percent tetrasodium EDDS.

Example 8

Methanol (500 ml, 390 g) and ethylenediamine (1 mole, 60.1 g) are mixed and allowed to cool to room temperature. Dimethyl maleate (1 mole, 144.1 g) is added slowly with stirring using a magnetic stir bar. The reaction mixture is stirred and kept at ambient temperature. The reaction mixture is diluted with methanol to a weight of 600 g. An aliquot of 100 g of the reaction mixture is placed in a flask and mixed with barium hydroxide (0.17 mole, 52.6 g) and water (11 mole, 200 g). The solution is then evaporated to dryness on a rotary evaporator at 100° C. The resulting solid is easily stored as a dry powder.

Example 9

Methanol (500 ml, 390 g) and ethylenediamine (1 mole, 60.1 g) are mixed and allowed to cool to room temperature. Dimethyl maleate (1 mole, 144.1 g) is added slowly with stirring using a magnetic stir bar. The reaction mixture is stirred and kept at ambient temperature. The reaction mixture is diluted with methanol to a weight of 600 g. An aliquot of 100 g of the reaction mixture is placed in a flask and mixed with aluminum hydroxide (0.17 mole, 8.67 g) and water (6 mole, 108 g). The solution is then evaporated to dryness on a rotary evaporator at 100° C. The resulting solid is easily stored as a dry powder for an extended time.

What is claimed is:

1. A process for preparing a polyamino monosuccinic acid, a salt or chelate thereof comprising
   (a) reacting a diester of maleic or fumaric acid or a mixture thereof with a polyamino compound in a primary alcohol as a solvent;
   (b) hydrolyzing the product obtained in step (a); and
   (c) separating the alcohol(s).
2. The process of claim 1 wherein the ester of maleic or fumaric acid is an alkyl ester of from 1 to 4 carbon atoms.
3. The process of claim 2 wherein the ester is a methyl or ethyl ester.
4. The process of claim 2 wherein the ester is a maleic acid ester.
5. The process of claim 4 wherein the ester is a methyl or ethyl ester.
6. The process of claim 1 wherein the polyamino compound is a diamino compound.
7. The process of claim 6 wherein the diamino compound is ethylenediamine.
8. The process of claim 1 wherein the primary alcohol is methanol, ethanol, 1-propanol or 1-butanol.
9. The process of claim 8 wherein the primary alcohol is methanol or ethanol.
10. The process of claim 9 wherein the primary alcohol is methanol.
11. The process of claim 1 wherein the primary alcohol is recycled from step (c) to step (a).
12. The process of claim 1 wherein the primary alcohol is separated by distillation.
13. The process of claim 1 wherein the hydrolysis in step (b) is performed under alkaline conditions.
14. The process of claim 13 wherein the hydrolysis is performed under aqueous conditions with a metal oxide or metal hydroxide.
15. The process of claim 14 wherein the metal oxide is alkali metal oxide or alkaline earth metal oxide.
16. The process of claim 14 wherein the metal hydroxide is alkali metal hydroxide or alkaline earth metal hydroxide.
17. The process of claim 16 wherein the metal hydroxide is sodium, potassium, or calcium hydroxide.
18. The process of claim 1 wherein the hydrolysis in step (b) is performed under acidic conditions.
19. The process of claim 1 wherein the separation of the alcohol is performed during the hydrolysis step (b).
20. The process of claim 1 wherein in step (a) methyl maleate is reacted with ethylenediamine in methanol.
21. The process of claim 20 wherein the hydrolysis in step (c) is performed in aqueous solution with sodium hydroxide or potassium hydroxide.

* * * * *